(12) United States Patent
Park

(10) Patent No.: US 11,230,575 B2
(45) Date of Patent: Jan. 25, 2022

(54) INSOLUBLE FUSION PROTEIN COMPRISING ANTIMICROBIAL PEPTIDE AND METHOD FOR PRODUCING ANTIMICROBIAL PEPTIDE USING SAME

(71) Applicant: Konkuk University Industrial Cooperation Corp., Seoul (KR)

(72) Inventor: Chan Kyu Park, Seoul (KR)

(73) Assignee: Konkuk University Industrial Cooperation Corp, Seoul (KR)

( * ) Notice: Subject to any disclaimer, the term of this patent is extended or adjusted under 35 U.S.C. 154(b) by 118 days.

(21) Appl. No.: 16/067,876

(22) PCT Filed: Feb. 26, 2016

(86) PCT No.: PCT/KR2016/001940
§ 371 (c)(1),
(2) Date: Jul. 3, 2018

(87) PCT Pub. No.: WO2017/131279
PCT Pub. Date: Aug. 3, 2017

(65) Prior Publication Data
US 2021/0032295 A1    Feb. 4, 2021

(30) Foreign Application Priority Data
Jan. 27, 2016 (KR) .................. 10-2016-0009970

(51) Int. Cl.
| | | |
|---|---|---|
| C07K 14/245 | (2006.01) | |
| A01N 33/08 | (2006.01) | |
| C12N 15/62 | (2006.01) | |
| C07K 14/47 | (2006.01) | |
| A61K 38/00 | (2006.01) | |
| C12N 15/09 | (2006.01) | |

(52) U.S. Cl.
CPC ............ C07K 14/245 (2013.01); A01N 33/08 (2013.01); C07K 14/4723 (2013.01); C12N 15/62 (2013.01); A61K 38/00 (2013.01); C07K 14/47 (2013.01); C07K 2319/00 (2013.01); C07K 2319/50 (2013.01); C07K 2319/60 (2013.01); C12N 15/09 (2013.01)

(58) Field of Classification Search
CPC .. C07K 14/245; C07K 2319/50; C07K 14/47; C07K 2319/60; C07K 2319/00; C07K 14/37; C07K 14/195; A01N 33/08; C12N 15/62; C12N 15/09; C12N 15/70; A61K 38/00

See application file for complete search history.

(56) References Cited

U.S. PATENT DOCUMENTS

2008/0280781 A1* 11/2008 Chen ..................... C12N 15/62
 506/14
2011/0009291 A1*  1/2011 Chen ................. C07K 14/4723
 506/14
2015/0051374 A1   2/2015 Liu et al.

FOREIGN PATENT DOCUMENTS

| KR | 10-2005-0016362 A | 2/2005 |
| KR | 10-0958095 B1     | 5/2010 |
| KR | 10-2012-0062504 A | 6/2012 |
| KR | 10-2015-0084152 A | 7/2015 |
| KR | 10-1550217 B1     | 9/2015 |
| KR | 10-1622373 B1     | 5/2016 |

OTHER PUBLICATIONS

Burgess, et al., Journal of Cell Biology, vol. 111, pp. 2129-2138 (Year: 1990).*
Chalfie et al., Photochemistry and Phtobiology 62(4): 651-656 (Year: 1995).*
Kobayashi, "Engineering a novel mulifunctional green fluorescent potein tag fora wide variety of protein research" PLoS One, vol. 3, Issue 12, e3822.
Cetinkaya "How do insertions affect grren fluorescent portein?" Chimcal Physics Letters, vol. 419, pp. 48-54 (2006).
Soundrarajan "Green fluorescent potein as a scaffold for high efficiency production of functional bacteriotoxic proteins in Escherichiacoli" Scientific Reports, vol. 6, Article No. 20661, internal pp. 1-10 (Feb. 11, 2016).
International Search Report PCT/ISA/210 for International Application No. PCT/KR2016/001940 dated Oct. 20, 2016.
Written Opinion of the International Searching Authority PCT/ISA/237 for International Application No. PCT/KR2016/001940 dated Oct. 20, 2016.

* cited by examiner

*Primary Examiner* — Phuong Huynh
(74) *Attorney, Agent, or Firm* — Harness, Dickey & Pierce, P.L.C.

(57) ABSTRACT

Disclosed is a method of producing an antimicrobial peptide wherein an antimicrobial peptide gene is fused with a green fluorescent protein gene expressed insolubly in *E. coli*, followed by introduction into *E. coli*, expression, and removal of the green fluorescent protein to yield the antimicrobial peptide. This method is capable of producing the antimicrobial peptide with high yield in a simple and economical manner and is thus effective at providing native antibiotics that can replace conventional antibiotics in pharmaceutical and feed industries, requiring the development of antibiotics having a new mechanism of action that can eradicate resistant strains due to the proliferation of multiple-drug-resistant microorganisms. Furthermore, the use of an amino acid cleavage process through acid treatment, instead of using conventional cyanogen bromide, is cost-effective for the purification of a target protein from an insoluble protein, can decrease the risk of processing, and enables rapid processing.

11 Claims, 15 Drawing Sheets

Specification includes a Sequence Listing.

[Figure 1A]

MHHHHHHHHQSKGEELFTGVVPILVELDGDVNGHKFSVRGEGEGDATNGKLTLKFICTTG
KLPVPWPTLVTTLGYGVQCFARYPDHIKRHDFFKSALPEGYVQERTISFKDDGTYKTRA
EVKFEGDTLVNRIELKGIDFKEDGNILGHKLEYNFNSHKVYITADKQKNGIKANFKIRHN
VEGGSGTMAMPMGSGGDGSVQLADHYQQNTPIGDDNHYLSTQSVLLKDPNEKRDHA
VLLEFVTAAGITHGKDELYKHHHHHHHH

[Figure 1B]
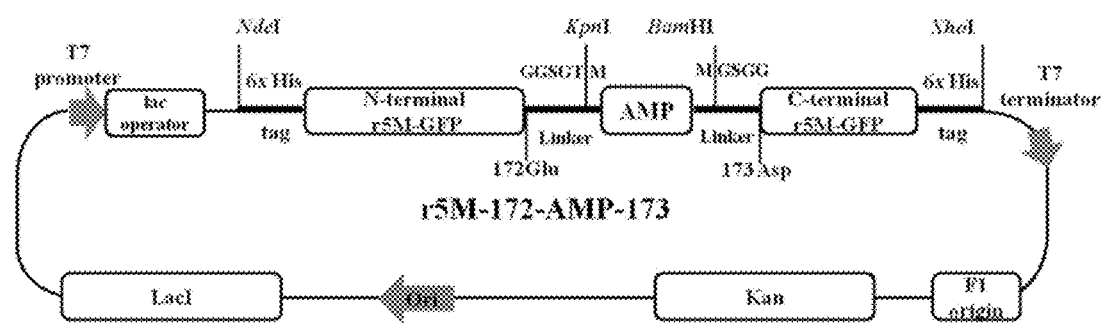

[Figure 1 C]
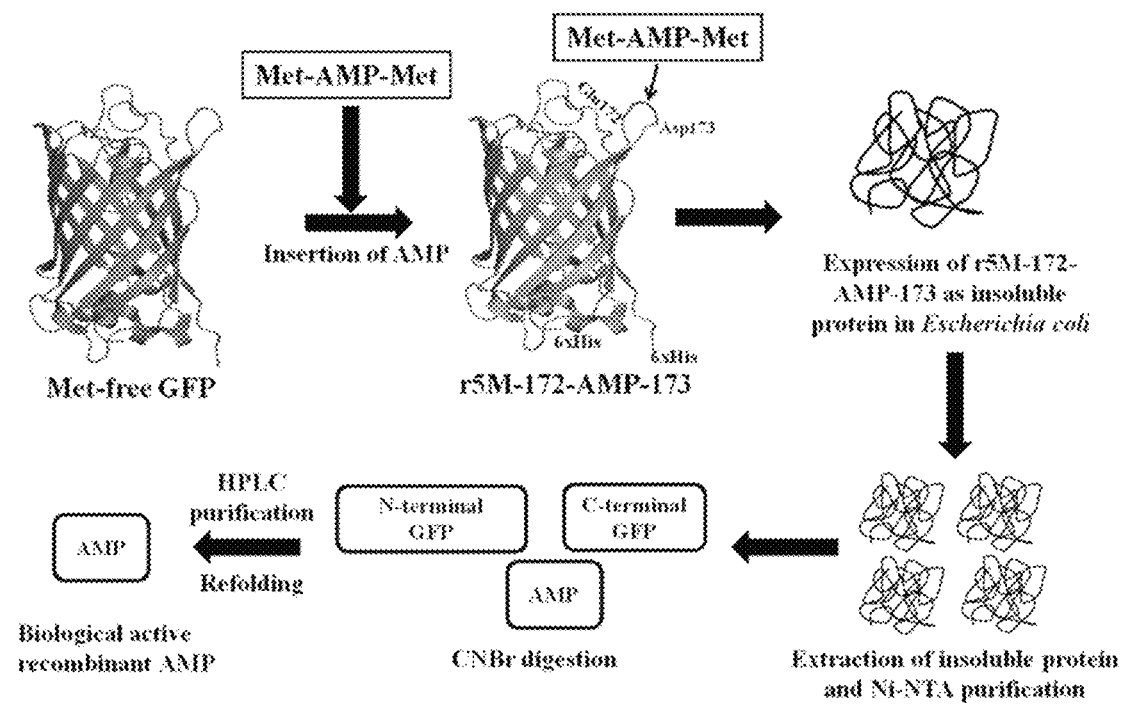

[Figure 2]

MHHHHHHHQSKGEELFTGVVPILVELDGDVNGHKFSVRGEGEGDATNGKLTLKFICTTG
KLPVPWPTLVTTLGYGVQCFARYPSHIKRHDFFKSALPEGYVQERTISFKDDGTYKTRA
EVKFEGDTLVNRIELKGIDFKEDGNILGHKLEYNPNSHKVYITADKQKNGIKANFKIRHN
VTCGSGTDPRGGRLCYCRRRFCVCVGRGDFRGGRLCYCRRRFCVCVGRGDFRGG
RLCYCRRRFCVCVGRGDPGSGCDGSVQLADHYQQNTPIGDDNHYLSTQSVLLKSPNE
KRDHAVLLEFVTAAGITHGKDELYKHHHHHHH

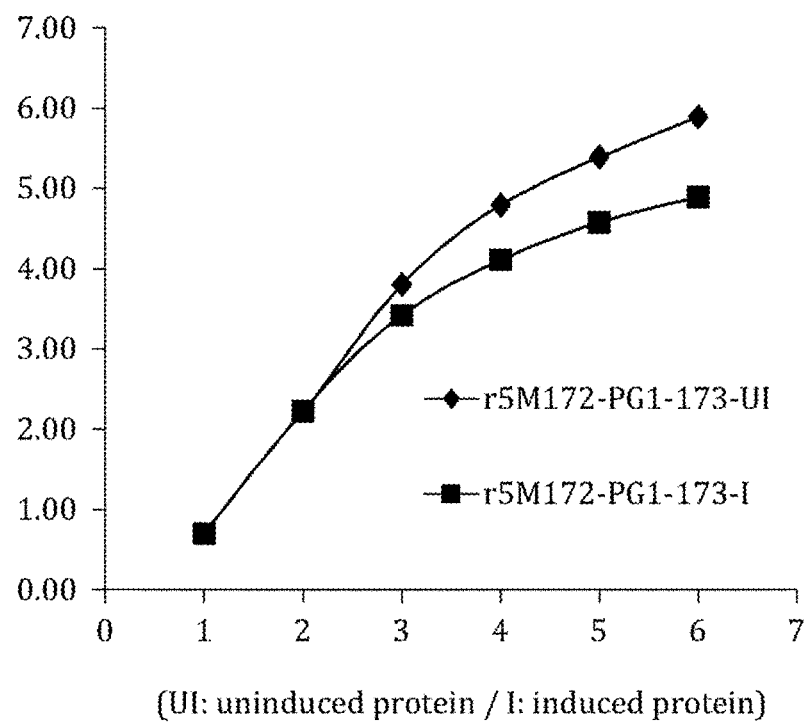
[Figure 3]
(UI: uninduced protein / I: induced protein)

[Figure 4A]
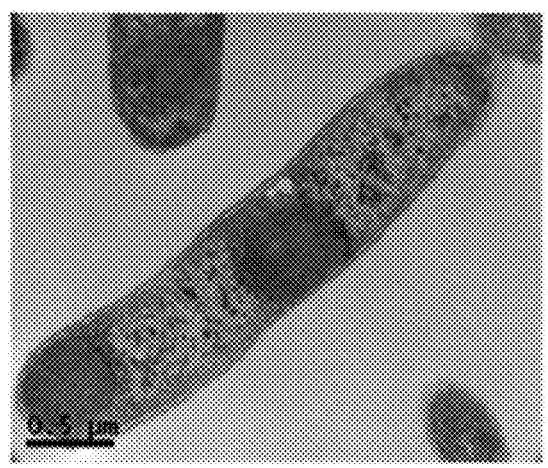

[Figure 4B]
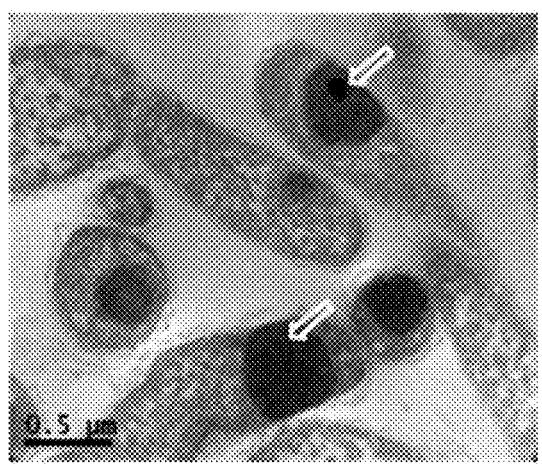

[Figure 4C]
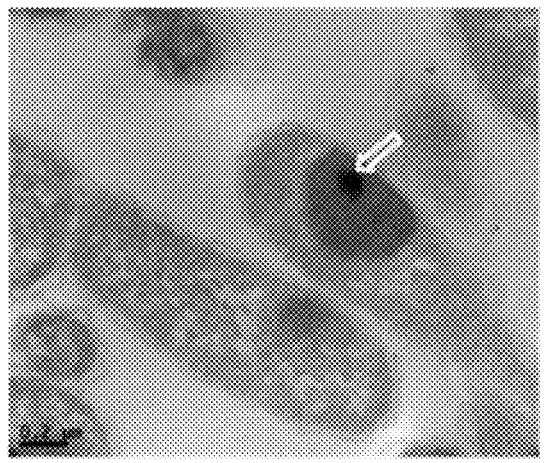

[Figure 4D]
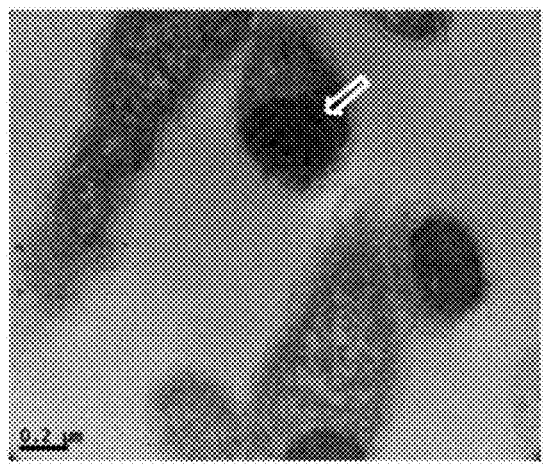

[Figure 5]
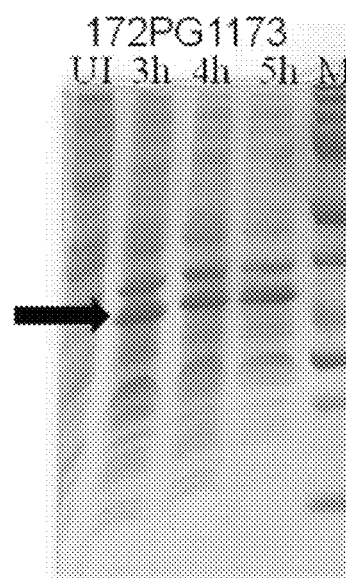
lane UI: uninduced protein sample
lane 3h to 5h: induced protein samples collected at 3h, 4h and 5h
lane M: molecular weight marker
arrow : expected size of 172PG1173

[Figure 6A]
172PG1173
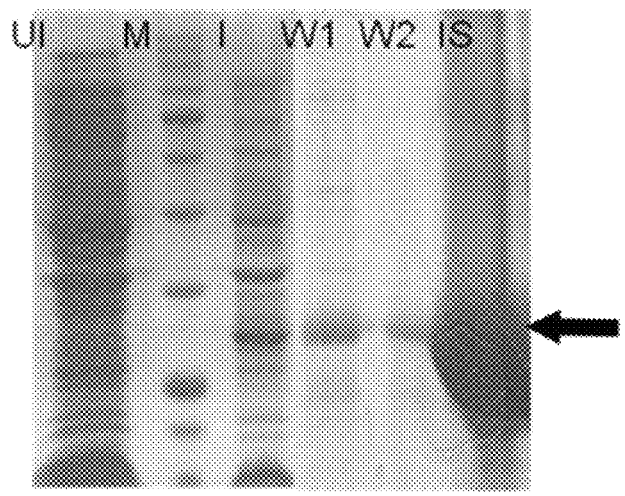
lane UI: uninduced protein
lane I: induced total cell protein after 5 hours expression
lane W1: insoluble protein after 1st washing step
lane W2: insoluble protein after 2nd washing step
lane IS: the final insoluble extracted protein
lane M: molecular weight marker
arrow : expected size of 172PG1173

[Figure 6B]
172PMAP36173
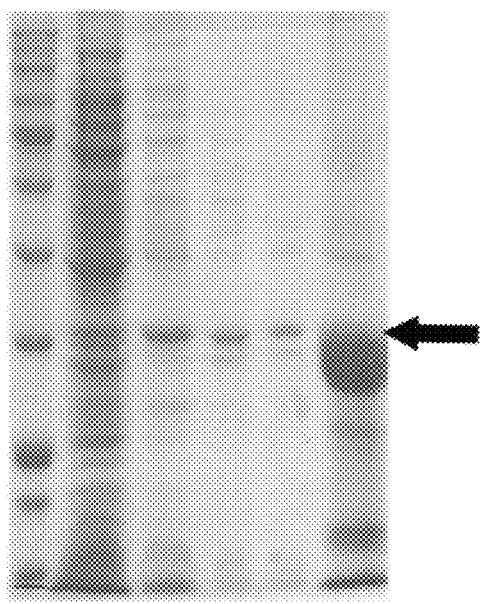
lane UI: uninduced protein
lane I: induced total cell protein after 5 hours expression
lane W1: insoluble protein after 1st washing step
lane W2: insoluble protein after 2nd washing step
lane IS: the final insoluble extracted protein
lane M: molecular weight marker
arrow : expected size of 172PMAP36173

[Figure 7A]
PG1
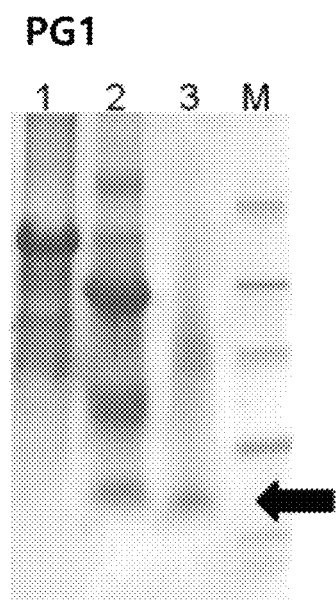
lane 1: affinity purification of insoluble protein
lane 2: CNBr digestion of purified insoluble protein
lane 3: final HPLC purification of PG1 and PMAP36
lane M: molecular weight marker
arrow: expected size of PG1 and PMAP36

[Figure 7B]
PMAP36
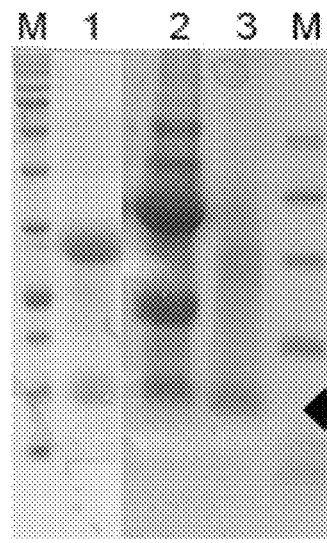
lane 1: affinity purification of insoluble protein
lane 2: CNBr digestion of purified insoluble protein
lane 3: final HPLC purification of PG1 and PMAP36
lane M: molecular weight marker
arrow: expected size of PG1 and PMAP36

[Figure 7C]
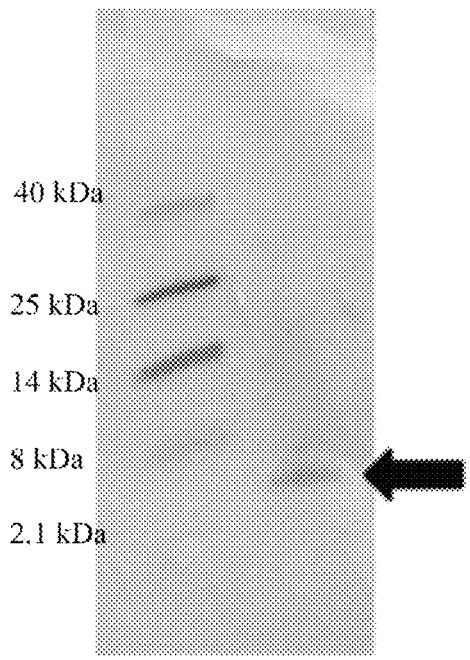
arrow : purified PG1

SEQUENCE LISTING

```
<160> NUMBER OF SEQ ID NOS: 24

<210> SEQ ID NO 1
<211> LENGTH: 57
<212> TYPE: DNA
<213> ORGANISM: Sus scrofa

<400> SEQUENCE: 1
agggagggtc gcctgtgcta ttgtaggcgt aggttctgcg tctgtgtcgg acgagga        57

<210> SEQ ID NO 2
<211> LENGTH: 108
<212> TYPE: DNA
<213> ORGANISM: Sus scrofa

<400> SEQUENCE: 2
ggacgattta gacggttgcg taagaagacc cgaaaacgtt tgaagaagat cgggaaggtt    60
ttgaagtgga ttcctcccat tgtcggctca ataccttgg gttgtggg                 108

<210> SEQ ID NO 3
<211> LENGTH: 30
<212> TYPE: DNA
<213> ORGANISM: Artificial Sequence
<220> FEATURE:
<223> OTHER INFORMATION: Synthesized PCR primer
```

<400> SEQUENCE: 3
catatgcatc accatcatca ccatcagagc                                    30

<210> SEQ ID NO 4
<211> LENGTH: 32
<212> TYPE: DNA
<213> ORGANISM: Artificial Sequence
<220> FEATURE:
<223> OTHER INFORMATION: Synthesized PCR primer

<400> SEQUENCE: 4
catggtacca gaaccacctt ccacgttatg ac                                 32

<210> SEQ ID NO 5
<211> LENGTH: 26
<212> TYPE: DNA
<213> ORGANISM: Artificial Sequence
<220> FEATURE:
<223> OTHER INFORMATION: Synthesized PCR primer

<400> SEQUENCE: 5
atgggatccg gtggcgatgg cagcgt                                        26

<210> SEQ ID NO 6
<211> LENGTH: 27
<212> TYPE: DNA
<213> ORGANISM: Artificial Sequence
<220> FEATURE:
<223> OTHER INFORMATION: Synthesized PCR primer

<400> SEQUENCE: 6
gtggtggtgc tcgagttatt aatggtg                                       27

<210> SEQ ID NO 7
<211> LENGTH: 37
<212> TYPE: DNA
<213> ORGANISM: Artificial Sequence
<220> FEATURE:
<223> OTHER INFORMATION: PCR primer

<400> SEQUENCE: 7
gcggttctgg tggtaccatg aggggaggtc gcctgtg                            37

<210> SEQ ID NO 8
<211> LENGTH: 34
<212> TYPE: DNA
<213> ORGANISM: Artificial Sequence
<220> FEATURE:
<223> OTHER INFORMATION: Synthesized PCR primer

<400> SEQUENCE: 8
gccaccggat cccattcctc gtccgacaca gacg                               34

<210> SEQ ID NO 9
<211> LENGTH: 38
<212> TYPE: DNA
<213> ORGANISM: Artificial Sequence
<220> FEATURE:
<223> OTHER INFORMATION: Synthesized PCR primer

<400> SEQUENCE: 9
gcggttctgg tggtaccatg ggacgattta gacggttg                           38

<210> SEQ ID NO 10
<211> LENGTH: 30

```
<212> TYPE: DNA
<213> ORGANISM: Artificial Sequence
<220> FEATURE:
<223> OTHER INFORMATION: PCR primer

<400> SEQUENCE: 10
caccggatcc catcccacaa cccaagggta                              30

<210> SEQ ID NO 11
<211> LENGTH: 63
<212> TYPE: DNA
<213> ORGANISM: Artificial Sequence
<220> FEATURE:
<223> OTHER INFORMATION: Synthesized PCR primer

<400> SEQUENCE: 11
ccgaggggag gtcgcctgtg ctattgtagg cgtaggttct gcgtctgtgt cggacgagga    60
gac                                                           63

<210> SEQ ID NO 12
<211> LENGTH: 63
<212> TYPE: DNA
<213> ORGANISM: Artificial Sequence
<220> FEATURE:
<223> OTHER INFORMATION: Synthesized PCR primer

<400> SEQUENCE: 12
tcctcgtccg acacagacgc agaacctacg cctacaatag cacaggcgac ctcccctcgg    60
ctg                                                           63

<210> SEQ ID NO 13
<211> LENGTH: 40
<212> TYPE: DNA
<213> ORGANISM: Artificial Sequence
<220> FEATURE:
<223> OTHER INFORMATION: Synthesized PCR primer

<400> SEQUENCE: 13
gtacccagga cctgccggga tccggtggcg atggcagcgt                   40

<210> SEQ ID NO 14
<211> LENGTH: 31
<212> TYPE: DNA
<213> ORGANISM: Artificial Sequence
<220> FEATURE:
<223> OTHER INFORMATION: Synthesized PCR primer

<400> SEQUENCE: 14
cagcatctgg gtaccagaac caccttccac g                            31

<210> SEQ ID NO 15
<211> LENGTH: 26
<212> TYPE: DNA
<213> ORGANISM: Artificial Sequence
<220> FEATURE:
<223> OTHER INFORMATION: Synthesized PCR primer

<400> SEQUENCE: 15
gcacgttatc cgtctcacat caaacg                                  26

<210> SEQ ID NO 16
<211> LENGTH: 26
<212> TYPE: DNA
<213> ORGANISM: Artificial Sequence
<220> FEATURE:
```

<223> OTHER INFORMATION: Synthesized PCR primer

<400> SEQUENCE: 16
cgtttgatgt gagacggata acgtgc                                          26

<210> SEQ ID NO 17
<211> LENGTH: 28
<212> TYPE: DNA
<213> ORGANISM: Artificial Sequence
<220> FEATURE:
<223> OTHER INFORMATION: Synthesized PCR primer

<400> SEQUENCE: 17
ctgctgaaat ctccgaacga aaaacgtg                                        28

<210> SEQ ID NO 18
<211> LENGTH: 28
<212> TYPE: DNA
<213> ORGANISM: Artificial Sequence
<220> FEATURE:
<223> OTHER INFORMATION: Synthesized PCR primer

<400> SEQUENCE: 18
cacgtttttc gttcggagat ttcagcag                                        28

<210> SEQ ID NO 19
<211> LENGTH: 843
<212> TYPE: DNA
<213> ORGANISM: Artificial Sequence
<220> FEATURE:
<223> OTHER INFORMATION: Synthesized; and Sus scrofa

<400> SEQUENCE: 19
catatgcatc accatcatca ccatcagagc aaaggcgaag aactgtttac cggcgtggtg     60
ccgattctgg tggaactgga tggcgatgtg aacggccata aatttagcgt gcgtggcgaa    120
ggcgaaggcg atgcgaccaa cggcaaactg accctgaaat ttatttgcac caccggtaaa    180
ctgccggtgc cgtggccgac cctggtgacc accctgggtt atggtgtgca gtgctttgca    240
cgttatccgg atcacatcaa acgtcatgat ttctttaaaa gcgcgctgcc ggaaggctat    300
gtgcaggaac gtaccattag ctttaaagat gatggcacct ataaaacccg tgcggaagtg    360
aaatttgaag cgatacccct ggtgaaccgt attgaactga aaggcattga ttttaaagaa    420
gatggcaaca ttctgggcca taaactggaa tataacttta cagccataaa agtgtatatt    480
accgcggata acagaaaaaa cggcattaaa gcgaacttta aaattcgtca taacgtggaa    540
ggtggttctg gtaccatgag gggaggtcgc ctgtgctatt gtaggcgtag gttctgcgtc    600
tgtgtcggac gaggaatggg atccggtggc gatggcagcg tgcagctggc ggatcattat    660
cagcagaaca ccccgattgg cgatgataac cattatctga gcacccagag cgtgctgctg    720
aaagatccga cgaaaaaacg tgatcacgcg gtgctgctgg aatttgtgac cgcggcgggc    780
attacccacg gcaaagatga actgtataaa catcaccatc atcaccatta ataactcgag    840
atc                                                                  843

<210> SEQ ID NO 20
<211> LENGTH: 891
<212> TYPE: DNA
<213> ORGANISM: Artificial Sequence
<220> FEATURE:
<223> OTHER INFORMATION: Synthesized; and Sus scrofa

<400> SEQUENCE: 20

```
catatgcatc accatcatca ccatcagagc aaaggcgaag aactgtttac cggcgtggtg      60
ccgattctgg tggaactgga tggcgatgtg aacggccata aatttagcgt gcgtggcgaa     120
ggcgaaggcg atgcgaccaa cggcaaactg accctgaaat ttatttgcac caccggtaaa     180
ctgccggtgc cgtggccgac cctggtgacc accctgggtt atggtgtgca gtgctttgca     240
cgttatccgg atcacatcaa acgtcatgat ttctttaaaa gcgcgctgcc ggaaggctat     300
gtgcaggaac gtaccattag ctttaaagat gatggcacct ataaaacccg tgcggaagtg     360
aaatttgaag gcgataccct ggtgaaccgt attgaactga aaggcattga ttttaaagaa     420
gatggcaaca ttctgggcca taaactggaa tataacttta cagccataaa agtgtatatt     480
accgcggata acagaaaaa cggcattaaa gcgaacttta aaattcgtca taacgtggaa      540
ggtggttctg gtaccatggg acgatttaga cggttgcgta agaagacccg aaaacgtttg     600
aagaagatcg ggaaggtttt gaagtggatt cctcccattg tcggctcaat acccttgggt     660
tgtgggatgg gatccggtgg cgatggcagc gtgcagctgg cggatcatta tcagcagaac     720
accccgattg cgatgataa ccattatctg agcacccaga gcgtgctgct gaaagatccg      780
aacgaaaaac gtgatcacgc ggtgctgctg aatttgtga ccgcggcggg cattacccac      840
ggcaaagatg aactgtataa acatcaccat catcaccatt ataactcga g               891
```

```
<210> SEQ ID NO 21
<211> LENGTH: 963
<212> TYPE: DNA
<213> ORGANISM: Artificial Sequence
<220> FEATURE:
<223> OTHER INFORMATION: Synthesized; and Sus scrofa

<400> SEQUENCE: 21
```

```
atgcatcacc atcatcacca tcagagcaaa ggcgaagaac tgtttaccgg cgtggtgccg      60
attctggtgg aactggatgg cgatgtgaac ggccataaat ttagcgtgcg tggcgaaggc     120
gaaggcgatg cgaccaacgg caaactgacc ctgaaattta tttgcaccac cggtaaactg     180
ccggtgccgt ggccgacccct ggtgaccacc ctgggttatg gtgtgcagtg ctttgcacgt    240
tatccgtctc acatcaaacg tcatgatttc tttaaaagcg cgctgccgga aggctatgtg     300
caggaacgta ccattagctt taaagatgat ggcacctata aaacccgtgc ggaagtgaaa     360
tttgaaggcg ataccctggt gaaccgtatt gaactgaaag gcattgattt taaagaagat     420
ggcaacattc tgggccataa actggaatat aactttaaca gccataaagt gtatattacc     480
gcggataaac agaaaaacgg cattaaagcg aactttaaaa ttcgtcataa cgtggaaggt     540
ggttctggta ccgacccgag gggaggtcgc ctgtgctatt gtaggcgtag gttctgcgtc     600
tgtgtcggac gaggagaccc gagggaggt cgcctgtgct attgtaggcg taggttctgc      660
gtctgtgtcg gacgaggaga cccgaggga ggtcgcctgt gctattgtag gcgtaggttc      720
tgcgtctgtg tcggacgagg agacccggga tccggtggcg atggcagcgt gcagctggcg     780
gatcattatc agcagaacac cccgattggc gatgataacc attatctgag cacccagagc     840
gtgctgctga atctccgaa cgaaaaacgt gatcacgcgg tgctgctgga atttgtgacc      900
gcggcgggca ttacccacgg caaagatgaa ctgtataaac accatcacca ccatcactaa     960
taa                                                                  963
```

```
<210> SEQ ID NO 22
<211> LENGTH: 9
<212> TYPE: DNA
```

```
<213> ORGANISM: Artificial Sequence
<220> FEATURE:
<223> OTHER INFORMATION: Synthesized

<400> SEQUENCE: 22 ggtggttct                                                                    9

<210> SEQ ID NO 23
<211> LENGTH: 12
<212> TYPE: DNA
<213> ORGANISM: Artificial Sequence
<220> FEATURE:
<223> OTHER INFORMATION: Synthesized

<400> SEQUENCE: 23
ggatccggtg gc                                                               12

<210> SEQ ID NO 24
<211> LENGTH: 319
<212> TYPE: PRT
<213> ORGANISM: Artificial Sequence
<220> FEATURE:
<223> OTHER INFORMATION: Synthesized; and Sus scrofa

<400> SEQUENCE: 24
```

Met His His His His His His Gln Ser Lys Gly Glu Glu Leu Phe Thr
1               5                   10                  15

Gly Val Val Pro Ile Leu Val Glu Leu Asp Gly Asp Val Asn Gly His
            20                  25                  30

Lys Phe Ser Val Arg Gly Glu Gly Glu Gly Asp Ala Thr Asn Gly Lys
        35                  40                  45

Leu Thr Leu Lys Phe Ile Cys Thr Thr Gly Lys Leu Pro Val Pro Trp
    50                  55                  60

Pro Thr Leu Val Thr Thr Leu Gly Tyr Gly Val Gln Cys Phe Ala Arg
65                  70                  75                  80

Tyr Pro Ser His Ile Lys Arg His Asp Phe Phe Lys Ser Ala Leu Pro
                85                  90                  95

Glu Gly Tyr Val Gln Glu Arg Thr Ile Ser Phe Lys Asp Asp Gly Thr
            100                 105                 110

Tyr Lys Thr Arg Ala Glu Val Lys Phe Glu Gly Asp Thr Leu Val Asn
        115                 120                 125

Arg Ile Glu Leu Lys Gly Ile Asp Phe Lys Glu Asp Gly Asn Ile Leu
    130                 135                 140

Gly His Lys Leu Glu Tyr Asn Phe Asn Ser His Lys Val Tyr Ile Thr
145                 150                 155                 160

Ala Asp Lys Gln Lys Asn Gly Ile Lys Ala Asn Phe Lys Ile Arg His
                165                 170                 175

Asn Val Glu Gly Gly Ser Gly Thr Asp Pro Arg Gly Arg Leu Cys
            180                 185                 190

Tyr Cys Arg Arg Arg Phe Cys Val Cys Val Gly Arg Gly Asp Pro Arg
        195                 200                 205

Gly Gly Arg Leu Cys Tyr Cys Arg Arg Phe Cys Val Cys Val Gly
    210                 215                 220

Arg Gly Asp Pro Arg Gly Gly Arg Leu Cys Tyr Cys Arg Arg Arg Phe
225                 230                 235                 240

Cys Val Cys Val Gly Arg Gly Asp Pro Gly Ser Gly Gly Asp Gly Ser
                245                 250                 255

Val Gln Leu Ala Asp His Tyr Gln Gln Asn Thr Pro Ile Gly Asp Asp

```
                    260                 265                 270
Asn His Tyr Leu Ser Thr Gln Ser Val Leu Leu Lys Ser Pro Asn Glu
            275                 280                 285

Lys Arg Asp His Ala Val Leu Leu Glu Phe Val Thr Ala Ala Gly Ile
        290                 295                 300

Thr His Gly Lys Asp Glu Leu Tyr Lys His His His His His His
305                 310                 315
```

INSOLUBLE FUSION PROTEIN COMPRISING ANTIMICROBIAL PEPTIDE AND METHOD FOR PRODUCING ANTIMICROBIAL PEPTIDE USING SAME

CROSS-REFERENCE TO RELATED APPLICATIONS

This application is a national phase under 35 U.S.C. § 371 of PCT International Application No. PCT/KR2016/001940 which has an International filing date of Feb. 26, 2016, which claims priority to Korean Application No. 10-2016-0009970, filed Jan. 27, 2016, the entire contents of each of which are hereby incorporated by reference.

SEQUENCE LISTING

This application is being filed electronically via the USPTO EFS-WEB server, as authorized and set forth in MPEP § 502.5 and this electronic filing includes an electronically submitted sequence listing. The entire content of this sequence listing is hereby incorporated by reference into the specification of this application. The sequence listing is identified on the electronically filed ASII(.txt) text file as follows:

| File Name | Date of Creation | Size |
|---|---|---|
| 17558-000018-US-NP_SequenceList | Aug. 24, 2020 | 9.370 bytes |

TECHNICAL FIELD

The present invention relates to a fusion protein comprising a green fluorescent protein (GFP) and an antimicrobial peptide (AMP) binding to each other and a method of mass-producing an antimicrobial peptide using the same, and more particularly to a method of mass-producing an antimicrobial peptide in a manner in which an antimicrobial peptide is fused with a green fluorescent protein that is expressed insolubly in Escherichia coli (E. coli), followed by introduction into E. coli, expression and then removal of the green fluorescent protein to thus obtain the antimicrobial peptide.

BACKGROUND ART

All organisms, ranging from microorganisms to higher organisms, have their own unique defense systems to protect themselves from external harmful environments. Moreover, it is known that not only microorganisms but also mycelia produce antimicrobial peptides, which are self-defense substances that exhibit antimicrobial activity, and thus have an innate immune system, thereby protecting themselves from external harmful factors before the antigen-antibody reaction.

Meanwhile, humans have developed and used many kinds of antibiotics since penicillin, but recently, strains resistant to such antibiotics have emerged at an increasingly rapid rate, unlike in the past. Particularly, multiple-drug-resistant microorganisms that manifest resistance to two or more different antibiotics or antimicrobials are proliferating, and it is urgent to develop antibiotics having a new mechanism of action that is capable of eradicating these resistant strains.

Thereby, native antimicrobial peptides have emerged as candidates for new antibiotics. Since they exhibit antimicrobial activity through the mechanism of an action different from that of conventional compound antibiotics, the problem of strains resistant to the antibiotics is considered to have been solved.

Accordingly, many attempts have been made to use native antimicrobial peptides without change or to synthesize analogs. However, since antimicrobial peptides increase not only antimicrobial activity, but also erythrocyte hemolysis, which is a measure of cytotoxicity, many limitations are imposed on real-world application thereof.

Moreover, technology for mass production, which is regarded as most important in terms of commercialization of antimicrobial peptides, has been variously studied but has not yet become industrially viable. This is because the production of antimicrobial peptides through chemical synthesis is not economical and the production of antimicrobial peptides through genetic engineering techniques using microorganisms is economical but the expressed antimicrobial peptides inhibit the growth of host microorganisms, undesirably resulting in very low peptide production yield.

Therefore, the present inventors have ascertained that the expression of a fusion protein, configured such that a green fluorescent protein expressed insolubly in E. coli binds as a scaffold to an antimicrobial peptide, is induced using an E. coli expression system in which gene manipulation is easy and which is economical, after which the antimicrobial peptide is isolated from the fusion protein, thus obtaining the peptide to thereby solve the problem in which the peptide production yield is decreased due to the deterioration of production of antimicrobial peptide through protein hydrolysis and due to the inhibition of growth of E. coli by the antimicrobial peptide, ultimately enabling mass production of the antimicrobial peptide in a simple and economical manner, thus culminating in the present invention.

The related art includes Korean Patent No. 10-0958095 (Method for the mass expression of an antimicrobial peptide using a translational coupling system), Korean Patent Application Publication No. 10-2012-0062504 (Multimeric antimicrobial peptide expressed on cell surface), etc.

DISCLOSURE

Technical Problem

Accordingly, the present invention is intended to provide a method of producing an antimicrobial peptide with high yield in a simple and economical manner by producing the antimicrobial peptide using an insoluble green fluorescent protein scaffold and using an E. coli expression system.

Technical Solution

Therefore, the present invention provides an insoluble fusion protein, comprising an antimicrobial peptide that is able to be activated through cleavage using acid treatment and a green fluorescent protein binding to each other.

The antimicrobial peptide may be continuously arranged, and an Asp-Pro amino acid sequence may be connected to an N-terminus or C-terminus of the continuously arranged antimicrobial peptide or a linkage portion thereof. The continuously arranged antimicrobial peptide may be present in three copies. The Asp-Pro amino acid sequence may be cleaved through acid treatment, and the acid treatment may be performed by adding HCl.

In addition, the present invention provides an insoluble fusion protein comprising the amino acid sequence of SEQ ID NO:24.

In addition, the present invention provides a gene encoding the above insoluble fusion protein and comprising the base sequence of SEQ ID NO:21.

In addition, the present invention provides a transformant, configured such that the recombinant expression vector is introduced into host cells. The host cells may be E. coli.

In addition, the present invention provides a method of producing an antimicrobial peptide, comprising: (1) incubating a recombinant transformant comprising the base sequence of SEQ ID NO:21 in a culture medium; (2) recovering the transformant from the culture medium; (3) obtaining a protein from the transformant; and (4) subjecting the protein to acid treatment to thus separate the antimicrobial peptide.

The protein may be expressed in the form of inclusion bodies.

The antimicrobial peptide may be continuously arranged, and an Asp-Pro amino acid sequence may be connected to an N-terminus or C-terminus of the continuously arranged antimicrobial peptide or a linkage portion thereof. The continuously arranged antimicrobial peptide may be present in three copies. The Asp-Pro amino acid sequence may be cleaved through acid treatment, and the acid treatment may be performed by the addition of HCl.

Advantageous Effects

According to the present invention, a method of mass-producing an antimicrobial peptide with high yield in a simple and economical manner is provided, and thus native antimicrobial peptides can be effectively utilized in pharmaceutical and feed industries under current conditions, in which the development of new antibiotics is urgent due to the proliferation of multiple-drug-resistant microorganisms.

Also according to the present invention, the use of an amino acid cleavage process through acid treatment, in lieu of using conventional cyanogen bromide, is cost-effective for the purification of a target protein from an insoluble protein, can decrease the risk of processing, and enables rapid processing.

DESCRIPTION OF DRAWINGS

FIG. 1A schematically shows a recombinant vector encoding a fusion protein (SEQ ID NO: 24) comprising an insoluble green fluorescent protein and an antimicrobial peptide;

FIG. 1B shows the amino acid sequence of recombinant r5M-172AMP173 [underline: r5M-GFP sequence; black shade: linker sequence and methionine moiety; gray shade: amino acid sequence site of AMP (AMP represented as a gray shade is not an amino acid sequence but is an abbreviation of an antimicrobial peptide)];

FIG. 1C schematically shows the purification of an antimicrobial peptide from an insoluble green fluorescent protein;

FIG. 2 shows the amino acid sequence of recombinant r5M-172(PG1)$_3$173 (SEQ ID NO: 24) (underline: r5M-GFP sequence; underline in gray shade: moiety where aspartic acid is substituted with serine; black shade: linker sequence and Asp-Pro binding site; no underline in gray shade: amino acid sequence of PG1);

FIG. 3 is a graph showing the growth curves of E. coli in which protein expression is induced and is not induced in E. coli into which a pET30b expression vector inserted with an r5M-172PG1173 gene is introduced, as measured through optical density;

FIG. 4A is an electron microscope image, showing that a protein (arrow) produced from a transformant inserted with an r5M-172PG1173 gene is provided in the form of inclusion bodies;

FIGS. 4B, 4C and 4D are electron microscope images after immunochemical labeling, showing that the protein (arrow) produced from a transformant inserted with an r5M-172PG1173 gene is provided in the form of inclusion bodies;

FIG. 5 shows the results of SDS-PAGE for the r5M-172PG1173 protein production over time (3 h, 4 h, 5 h) of a pET30b expression vector inserted with an r5M-172PG1173 gene in E. coli, as confirmed using a whole-cell protein sample;

FIG. 6A shows the expressed r5M-172PG1173 protein, as confirmed through SDS-PAGE at individual steps;

FIG. 6B shows the r5M-172PMAP36173 protein, as confirmed through SDS-PAGE at individual steps;

FIGS. 7A and 7B show the results of analysis of the purity of protein samples extracted at individual steps for the protein purification through tris-tricine SDS-PAGE; and FIG. 7C shows the results of western blot assay of purified PG1.

BEST MODE

Hereinafter, a detailed description will be given of the present invention.

The present invention addresses an insoluble fusion protein, configured such that an antimicrobial peptide (AMP), which may be activated through cleavage using acid treatment, and a green fluorescent protein (GFP) bind to each other. In order to prepare the insoluble fusion protein, the green fluorescent protein may be used as the scaffold for the antimicrobial peptide. The expression of the structure of the insoluble fusion protein in which the green fluorescent protein and the antimicrobial peptide bind to each other is induced, thus preventing damage to the antimicrobial peptide and minimizing the growth-inhibiting effect of the expression of the antimicrobial peptide on the host, thereby preventing the problem in which the peptide production yield is lowered due to the inhibition of host growth.

In an embodiment of the present invention, the antimicrobial peptide may be continuously arranged, and an Asp-Pro [aspartic acid-proline, DP] amino acid sequence may be connected to an N-terminus or C-terminus of the continuously arranged antimicrobial peptide or a linkage portion thereof. The continuously arranged antimicrobial peptide may be present in three copies. The Asp-Pro amino acid sequence may be cleaved through acid treatment. The acid treatment may be performed by adding HCl.

In addition, the present invention addresses a green fluorescent protein comprising the amino acid sequence of SEQ ID NO:24.

In order to manufacture the green fluorescent protein (hereinafter, referred to as "GFP"), mutation may be caused from 218$^{th}$ methionine (M218) to the alanine position in the amino acid sequence of GFP. Mutation may also be caused in all of the next internal methionine (Met) sites to thus induce methionine-deleted GFP (hereinafter, referred to as "r5M-GFP"). Furthermore, the 76$^{th}$ and 204$^{th}$ aspartic acid (D76, D204) positions may be substituted with serine (Ser, S).

In the insertion of r5M-GFP with the antimicrobial peptide, r5M-GFP may be cloned into a pET30b vector using NdeI and XhoI restriction enzyme sites, which may be performed through separation using a restriction enzyme and ligation using T4 ligase, and a detailed description thereof is as follows.

An N-terminal fragment may be prepared in a manner in which primer design is carried out using an r5M-GFP-inserted pET30b vector as a DNA template such that an NdeI (including a start codon) restriction enzyme site and His-Tag are positioned in the 5' direction and such that a linker (including a KpnI restriction enzyme site) next to the 172$^{nd}$ amino acid and methionine are positioned in the 3' direction, after which PCR is performed. A C-terminal fragment may be amplified by performing primer design such that methionine, a linker and the 173$^{rd}$ amino acid are positioned in the 5' direction and such that His-Tag, a stop codon and an XhoI restriction enzyme site are positioned in the 3' direction, as described above.

A primer, comprising the base sequence encoding the KpnI restriction enzyme site, the linker (including the KpnI restriction enzyme site) and methionine in the 5' direction and comprising the base sequence encoding methionine, the BamHI restriction enzyme site and the linker (including the BamHI restriction enzyme site) in the 3' direction, is designed using a gene encoding PG1 or PMAP36 as a DNA template, after which PCR may be performed.

When each gene of PG1 or PMAP36 amplified through PCR and two fragments amplified from r5M-GFP are amplified through overlap PCR, a gene (r5M-172-PG1-173 or r5M-172-PMAP-173) comprising the sequence encoding the antimicrobial peptide may be obtained. This is considered to be possible because individual fragments and genes have complementary base sequences for the methionine and the linker added in the previous PCR step (hereinafter, the structure of FIG. 1A, comprising the antimicrobial peptide binding to GFP, is represented as "r5M-172AMP173").

The r5M-172-PG1-173 or r5M-172-PMAP-173 gene may be obtained from agarose gel through gel extraction after PCR. Thereafter, the gene is cleaved with the NdeI and XhoI restriction enzymes, ligated using T4 ligase to the pET30b vector cleaved with the same two restriction enzymes, and is then transformed, thereby completing cloning (FIG. 1B).

In the above system, in which the gene is inserted into r5M-GFP, cloning may be performed through overlap PCR, which may require several PCR processes and gel extractions following individual PCR processes.

After the cloning, the vector obtained from the clone is cleaved using KpnI and BamHI restriction enzymes, whereby the inserted gene may be separated. For the gene to be cloned, primer design is carried out in the same manner as in the PG1 and PMAP36 genes, followed by PCR amplification and then cleavage with KpnI and BamHI restriction enzymes, whereby the inserted gene is subjected to ligation to the separated vector, thus simplifying the cloning process. Preferably, the restriction enzymes contained in the r5M-172AMP173 gene may be arranged in the sequence of NdeI, KpnI, BamHI and XhoI.

In addition, the present invention addresses a gene encoding the above green fluorescent protein and comprising the base sequence of SEQ ID NO:21.

In addition, the present invention addresses a recombinant expression vector, containing the above gene.

The recombinant gene (r5-M172AMP173) may be inserted into the NdeI and XhoI restriction enzyme sites of the pET30b expression vector. As such, in order to attach a histidine tag (His-Tag) to both termini of r5M-172AMP173, a His-Tag sequence may be added upon primer design for PCR. His-Tag indicates multiple histidines attached to the terminus of the recombinant protein. When using the selective binding ability of histidine to metal ions, the recombinant protein may be easily separated and purified.

Histidine, which is an amino acid having an imidazole group, may easily bind to bivalent metal ions such as $Ni^{2+}$ or $Fe^{2+}$. Since the attachment of His-Tag has to be taken into consideration from the step of preparing an expression vector of the recombinant protein, multiple histidines are expressed at the front or back site of the recombinant protein base sequence, and the number of histidines that are expressed may be 6 or more.

In addition, the present invention addresses a transformant in which the recombinant expression vector is introduced into host cells. The host cells may be E. coli, particularly E. coli BL21.

In addition, the present invention addresses a method of producing an antimicrobial peptide, comprising the steps of (1) incubating a recombinant transformant comprising the base sequence of SEQ ID NO:21 in a culture medium; (2) recovering the transformant from the culture medium; (3) obtaining a protein from the transformant; and (4) subjecting the protein to acid treatment to thus separate the antimicrobial peptide. The protein may be an insoluble protein.

In the step (1), the transformant may be E. coli BL21, and may be incubated in 1 L of an LB (Luria-Bertani) medium at 37° C., and protein expression may be induced by the addition of IPTG (Isopropyl β-D thiogalactoside).

In the step (2), the recovering may be performed using a centrifuge.

In an embodiment of the present invention, the insoluble protein may be expressed in the form of inclusion bodies.

In order to extract the insoluble protein, cells are disrupted using a sonicator, and the disrupted lysate is centrifuged to thus obtain a soluble fraction and an insoluble fraction. The insoluble fraction may be resuspended in a lysis buffer, and may then be added with a lysozyme to thus destroy the cell walls, and DNA is cleaved with DNase, followed by centrifugation, thereby separating the insoluble protein expressed in the form of inclusion bodies.

In order to increase the yield of the separated insoluble protein, a washing step for removing cell walls, cell debris and gDNA may be performed using a sodium phosphate buffer containing lysozyme and DNase.

The insoluble protein is expressed in the form of inclusion bodies, and thus the inhibition of the growth of host cells due to the toxic action of the antimicrobial peptide may be minimized. Furthermore, easy degradation of a polypeptide having a small molecular weight, such as an antimicrobial peptide, by the protease present in the host cells may be prevented, thus increasing the production yield during the production of the antimicrobial peptide.

The insoluble protein expressed in the form of inclusion bodies is purified through nickel-nitrilotriacetic acid (Ni-NTA) column chromatography, and the eluted fraction may be analyzed through SDS-PAGE and dialyzed with deionized water as a dialysis solution. The dialysis is performed in order to remove urea, imidazole and NaCl, which are added during the purification, after which the insoluble protein is freeze-dried, thereby removing unnecessary water. When dialysis and freeze-drying are carried out in this way, the insoluble protein may be obtained at high concentration.

In an embodiment of the present invention, the antimicrobial peptide is continuously arranged, and the Asp-Pro amino acid sequence may be connected to the N-terminus or C-terminus of the continuously arranged antimicrobial peptide or the linkage portion thereof. The continuously arranged antimicrobial peptide may be present in three copies. The Asp-Pro amino acid sequence may be cleaved through acid treatment. The acid treatment may be performed by the addition of HCl.

The acid treatment is a process of cleaving an amino acid bond under acidic conditions, and is preferably carried out in an inexpensive manner because conventionally useful cyanogen bromide is problematic in that it must be used carefully due to the high toxicity thereof, and thus the processing speed is slow, and also in that it is expensive, and thus economic benefits are negated.

When the N-terminus and C-terminus located at both ends of the antimicrobial peptide (PG1, PMAP36) are cleaved, only the antimicrobial peptide may be obtained (FIG. 1C). Thereafter, the antimicrobial peptide may be purified through reverse-phase high-performance liquid chromatography (HPLC). The purified antimicrobial peptide may be refolded to the native state by the addition of a refolding buffer, and simultaneously, the refolding buffer may be replaced with deionized water through dialysis.

Meanwhile, antimicrobial peptides discovered in various organisms to date are categorized into three groups based on the structures thereof. The first is the cysteine-rich β-sheet peptide, the second is the α-helical amphipathic molecule, and the third is the proline-rich peptide. A variety of structures of these antimicrobial peptides are determined by peptide amino acid sequences, and such structures are known to be closely related to the antimicrobial activity of the peptides.

In the present invention, Protegrin 1 (PG1), which has a typical anti-parallel beta-hairpin structure stabilized by two disulfide bonds and was first discovered in pig leucocytes, is used. Furthermore, pig myeloid antibacterial peptide36 (PMAP36), having a helix structure, is used, but the present invention is not limited thereto.

In order to evaluate the antimicrobial activity of the purified antimicrobial peptides PG1 and PMAP36 according to the embodiment of the present invention, a spot-on-lawn test was carried out using *E. coli* ATCC 25922, *Pseudomonas aeruginosa* ATCC 27853, and *Staphylococcus aureus* ATCC 29213. Consequently, antimicrobial activity was exhibited. The results are shown in Table 1 below.

TABLE 1

Table. Antimicrobial activity assay for the recombinant AMP produced

| Antimicrobial peptides | Strains | | |
|---|---|---|---|
| | *Escherichia coli* ATCC 25922 | *Pseudomonas aeruginosa* ATCC 27853 | *Staphylococcus aureus* ATCC 29213 |
| PG1 | 7 µg/ml | 15 µg/ml | 10 µg/ml |
| PMAP36 | 10 µg/ml | 11 µg/ml | 9 µg/ml |

A better understanding will be given of the present invention through the following examples, which are merely set forth to illustrate but are not to be construed as limiting the scope of the present invention, as will be apparent to those skilled in the art.

EXAMPLE 1

DNA Amplification and Expression Vector Preparation for Production of Fusion Protein Comprising Insoluble Green Fluorescent Protein and Antimicrobial Peptide Binding to Each Other Using a gene encoding an antimicrobial peptide PG1 (SEQ ID NO:1) and a gene encoding PMAP36 (SEQ ID NO:2) as a DNA template, designed was each primer comprising the base sequence encoding a KpnI restriction enzyme site, a linker (including the KpnI restriction enzyme site) and methionine in the 5' direction and comprising the base sequence encoding methionine, a BamHI restriction enzyme site and a linker (including the BamHI restriction enzyme site) in the 3' direction, followed by PCR. The individual primer sequences necessary for amplification are shown in Table 2 below.

SEQ ID NO: 1
5'-AGGGGAGGTCGCCTGTGCTATTGTAGGCGTAGGTTCTGCGTCTGTGT

CGGACGAGGA-3';

SEQ ID NO: 2
5'-GGACGATTTAGACGGTTGCGTAAGAAGACCCGAAAACGTTTGAAGAA

GATCGGGAAGGTTTTGAAGTGGATTCCTCCCATTGTCGGCTCAATACCCT

TGGGTTGTGGG-3';

Also, in the insertion of the mutated r5M-GFP with the antimicrobial peptide, primers in the 5' direction and the 3' direction for the r5M-GFP gene and the antimicrobial peptide were designed. The individual primer sequences necessary for the amplification are shown in Table 2 below.

TABLE 2

| SEQ ID NO | GENE | Primer | Base sequence (5' → 3') |
|---|---|---|---|
| SEQ ID NO: 3 | r5M-GFP (1$^{st}$ codon to 172 position) | Forward | CATATGCATCACCATCATCACCATCAGAGC |
| SEQ ID NO: 4 | | Backward | CATGGTACCAGAACCACCTTCCACGTTATGAC |
| SEQ ID NO: 5 | r5M-GFP (173 position to end) | Forward | ATGGGATCCGGTGGCGATGGCAGCGT |
| SEQ ID NO: 6 | | Backward | GTGGTGGTGCTCGAGTTATTAATGGTG |
| SEQ ID NO: 7 | PG1 | Forward | GCGGTTCTGGTGGTACCATGAGGGGAGGTCGCCTGTG |
| SEQ ID NO: 8 | | Backward | GCCACCGGATCCCATTCCTCGTCCGACACAGACG |
| SEQ ID NO: 9 | PMAP36 | Forward | GCGGTTCTGGTGGTACCATGGGACGATTTAGACGGTTG |
| SEQ ID NO: 10 | | Backward | CACCGGATCCCATCCCACAACCCAAGGGTA |

In the primer sequence, the base sequence of SEQ ID NO:3 contains a restriction enzyme NdeI recognition sequence for binding to the expression vector pET30b and a 6× His-Tag sequence (5'-CATCACCATCATCACCAT-3')

for Ni-NTA column chromatography, and the base sequence of SEQ ID NO:4 and the base sequence of SEQ ID NO:5 contain an ATG codon encoding methionine for peptide cleavage through cyanogen bromide treatment. Also, the base sequence of SEQ ID NO:6 contains a restriction enzyme XhoI recognition sequence for binding to the expression vector pET30b, and the base sequences of SEQ ID NO:7 (annealing temperature: 57° C.) and SEQ ID NO:9 (annealing temperature: 50° C.) contain a restriction enzyme KpnI and an ATG codon for peptide cleavage through cyanogen bromide treatment. Also, the base sequences of SEQ ID NO:8 and SEQ ID NO:10 contain a restriction enzyme BamHI recognition sequence and an ATG codon for peptide cleavage through cyanogen bromide treatment. When the ATG codon encoding methionine was added as described above, the peptide bond directly after the methionine residue was cleaved upon treatment of cyanide bromide (CNBr) during subsequent isolation of the antimicrobial peptides PG1 and PMAP36 from the fusion protein, thereby isolating the antimicrobial peptide.

When each gene of PG1 or PMAP36 amplified through PCR and two fragments amplified from r5M-GFP are amplified through overlap PCR, a gene (r5M-172-PG1-173 or r5M-172-PMAP-173) comprising the sequence encoding the antimicrobial peptide may be obtained. This is possible because individual fragments and genes have complementary base sequences for the methionine and the linker added in the previous PCR step (hereinafter, the structure of FIG. 1A, comprising the antimicrobial peptide binding to GFP, is represented as "r5M-172AMP173").

In order to increase the expression of PG1, the number of copies was increased to 3, and thus recombination was attempted. Using the 5'-terminal forward primer of SEQ ID NO:11 and the 3'-terminal backward primer of SEQ ID NO:12, gene fragments of PG1 were amplified. Individual PG1 monomers were continuously connected using T4 DNA Ligase (NEB). A polymer [(PG1)$_3$] containing three continuous copies of PG1 was subjected to electrophoresis in 3% low melting agarose gel, and thus a DNA band having a 150 to 300 bp size was identified, followed by purification to (PG1)$_3$ using phenol-chloroform.

(5' → 3')
SEQ ID NO: 11
CCGAGGGGAGGTCGCCTGTGCTATTGTAGGCGTAGGTTCTGCGTCTG

TGTCGGACGAGGAGAC;

(5' → 3')
SEQ ID NO: 12
TCCTCGTCCGACACAGACGCAGAACCTACGCCTACAATAGCACAGGC

GACCTCCCCTCGGCTG;

The DNA fragments thus amplified were ligated and recombined, and the antimicrobial peptide PG1, PMAP36 or (PG1)$_3$ gene was inserted into the loop region between the 172$^{nd}$ position and the 173$^{rd}$ position in the amino acid sequence of GFP. In particular, the insertion of (PG1)$_3$ gene was performed using the primers of SEQ ID NO:13 and SEQ ID NO:14 (Table 3). Accordingly, (PG1)$_3$ was configured such that the Asp-Pro (aspartic acid-proline, DP) amino acid sequence was connected to the N-terminus or C-terminus of continuously arranged PG1 in the form of three copies or the linkage portion thereof.

TABLE 3

| SEQ ID NO | Gene | Primer | Base sequence (5' → 3') |
|---|---|---|---|
| SEQ ID NO: 13 | 172A1wNI-DP-For | Forward | GTACCCAGGACCTGCCGGGATCCGG TGGCGATGGCAGCGT |
| SEQ ID NO: 14 | 172A1wNI-DP-Rev | Backward | CAGCATCTGGGTACCAGAACCACCT TCCACG |

In order to separate PG1 through cleavage of the Asp-Pro site from the protein produced from the transformant inserted with (PG1)$_3$ gene, site-directed mutagenesis of r5M-GFP was performed before insertion of the (PG1)$_3$ gene. The 76$^{th}$ and 204$^{th}$ aspartic acid (D76, D204) positions of the recombinant gene correspond to the Asp-Pro binding site and are thus substituted with serine (Ser, S), thus preventing the cleavage of unnecessary binding sites during protein separation (FIG. 2). The primers used for the substitution are shown in Table 4 below. The 76$^{th}$ aspartic acid using the primers of SEQ ID NO:15 and SEQ ID NO:16 and the 204$^{th}$ aspartic acid using the primers of SEQ ID NO:17 and SEQ ID NO:18 were substituted with serine.

TABLE 4

| SEQ ID NO | Gene | Primer | Base sequence (5' → 3') |
|---|---|---|---|
| SEQ ID NO: 15 | r5M-76D-S-F | Forward | GCACGTTATCCGT CTCACATCAAACG |
| SEQ ID NO: 16 | r5M-76D-S-R | Backward | CGTTTGATGTGAG ACGGATAACGTGC |
| SEQ ID NO: 17 | r5M-204D-S-F | Forward | CTGCTGAAATCTC CGAACGAAAAACG TG |
| SEQ ID NO: 18 | r5M-204D-S-R | Backward | CACGTTYTTCGTT CGGAGATTTCAGC AG |

The recombinant gene thus obtained is represented as "r5M-172PG1173" (insertion of antimicrobial peptide PG1 gene), "r5M-172PMAP36173" (insertion of antimicrobial peptide PMAP36), and "r5M-172(PG1)$_3$173" (insertion of antimicrobial peptide (PG1)$_3$). The base sequence of the recombinant gene r5M-172PG1173 is SEQ ID NO:19, the base sequence of r5M-172PMAP36173 is SEQ ID NO:20, and the base sequence of r5M-172(PG1)$_3$173 is SEQ ID NO:21, as shown below.

(5' → 3')
SEQ ID NO: 19
CATATGCATCACCATCATCACCATCAGAGCAAAGGCGAAGAACTGTTT

ACCGGCGTGGTGCCGATTCTGGTGGAACTGGATGGCGATGTGAACGGCCAT

AAATTTAGCGTGCGTGGCGAAGGCGAAGGCGATGCGACCAACGGCAAACTG

ACCCTGAAATTTATTTGCACCACCGGTAAACTGCCGGTGCCGTGGCCGACC

CTGGTGACCACCCTGGGTTATGGTGTGCAGTGCTTTGCACGTTATCCGGAT

CACATCAAACGTCATGATTTCTTTAAAAGCGCGCTGCCGGAAGGCTATGTG

CAGGAACGTACCATTAGCTTTAAAGATGATGGCACCTATAAAACCCGTGCG

-continued

```
GAAGTGAAATTTGAAGGCGATACCCTGGTGAACCGTATTGAACTGAAAGGC

ATTGATTTTAAAGAAGATGGCAACATTCTGGGCCATAAACTGGAATATAAC

TTTAACAGCCATAAAGTGTATATTACCGCGGATAAACAGAAAAACGGCATT

AAAGCGAACTTTAAAATTCGTCATAACGTGGAAGGTGGTTCTGGTACCATG

AGGGGAGGTCGCCTGTGCTATTGTAGGCGTAGGTTCTGCGTCTGTGTCGGA

CGAGGAATGGGATCCGGTGGCGATGGCAGCGTGCAGCTGGCGGATCATTAT

CAGCAGAACACCCCGATTGGCGATGATAACCATTATCTGAGCACCCAGAGC

GTGCTGCTGAAAGATCCGAACGAAAAACGTGATCACGCGGTGCTGCTGGAA

TTTGTGACCGCGGCGGGCATTACCCACGGCAAAGATGAACTGTATAAACAT

CACCATCATCACCATTAATAACTCGAGATC;

(5' → 3')
                                           SEQ ID NO: 20
CATATGCATCACCATCATCACCATCAGAGCAAAGGCGAAGAACTGTTT

ACCGGCGTGGTGCCGATTCTGGTGGAACTGGATGGCGATGTGAACGGCCAT

AAATTTAGCGTGCGTGGCGAAGGCGAAGGCGATGCGACCAACGGCAAACTG

ACCCTGAAATTTATTTGCACCACCGGTAAACTGCCGGTGCCGTGGCCGACC

CTGGTGACCACCCTGGGTTATGGTGTGCAGTGCTTTGCACGTTATCCGGAT

CACATCAAACGTCATGATTTCTTTAAAAGCGCGCTGCCGGAAGGCTATGTG

CAGGAACGTACCATTAGCTTTAAAGATGATGGCACCTATAAAACCCGTGCG

GAAGTGAAATTTGAAGGCGATACCCTGGTGAACCGTATTGAACTGAAAGGC

ATTGATTTTAAAGAAGATGGCAACATTCTGGGCCATAAACTGGAATATAAC

TTTAACAGCCATAAAGTGTATATTACCGCGGATAAACAGAAAAACGGCATT

AAAGCGAACTTTAAAATTCGTCATAACGTGGAAGGTGGTTCTGGTACCATG

GGACGATTTAGACGGTGCGTAAGAAGACCCGAAAACGTTTGAAGAAGATCG

GGAAGGTTTTGAAGTGGATTCCTCCCATTGTCGGCTCAATACCCTTGGGTT

GTGGGATGGGATCCGGTGGCGATGGCAGCGTGCAGCTGGCGGATCATTATC

AGCAGAACACCCCGATTGCGATGATAACCATTATCTGAGCACCCAGAGCGT

GCTGCTGAAAGATCCGAACGAAAAACGTGATCACGCGGTGCTGCTGGAATT

TGTGACCGCGGCGGGCATTACCCACGGCAAAGATGAACTGTATAAACATCA

CCATCATCACCATTAATAACTCGAG;

(5' → 3')
                                           SEQ ID NO: 21
ATGCATCACCATCATCACCATCAGAGCAAAGGCGAAGAACTGTTTACC

GGCGTGGTGCCGATTCTGGTGGAACTGGATGGCGATGTGAACGGCCATAAA

TTTAGCGTGCGTGGCGAAGGCGAAGGCGATGCGACCAACGGCAAACTGACC

CTGAAATTTATTTGCACCACCGGTAAACTGCCGGTGCCGTGGCCGACCCTG

GTGACCACCCTGGGTTATGGTGTGCAGTGCTTTGCACGTTATCCGTCTCAC

ATCAAACGTCATGATTTCTTTAAAAGCGCGCTGCCGGAAGGCTATGTGCAG

GAACGTACCATTAGCTTTAAAGATGATGGCACCTATAAAACCCGTGCGGAA

GTGAAATTTGAAGGCGATACCCTGGTGAACCGTATTGAACTGAAAGGCATT

GATTTTAAAGAAGATGGCAACATTCTGGGCCATAAACTGGAATATAACTTT

AACAGCCATAAAGTGTATATTACCGCGGATAAACAGAAAAACGGCATTAAA
```

```
GCGAACTTTAAAATTCGTCATAACGTGGAAGGTGGTTCTGGTACCGACCCG

AGGGGAGGTCGCCTGTGCTATTGTAGGCGTAGGTTCTGCGTCTGTGTCGGA

CGAGGAGACCCGAGGGGAGGTCGCCTGTGCTATTGTAGGCGTAGGTTCTGC

GTCTGTGTCGGACGAGGAGACCCGAGGGGAGGTCGCCTGTGCTATTGTAGG

CGTAGGTTCTGCGTCTGTGTCGGACGAGGAGACCCGGGATCCGGTGGCGAT

GGCAGCGTGCAGCTGGCGGATCATTATCAGCAGAACACCCCGATTGGCGAT

GATAACCATTATCTGAGCACCCAGAGCGTGCTGCTGAAATCTCCGAACGAA

AAACGTGATCACGCGGTGCTGCTGGAATTTGTGACCGCGGCGGGCATTACC

CACGGCAAAGATGAACTGTATAAACACCATCACCACCATCACTAATAA;
```

The base sequences of SEQ ID NO:19 to SEQ ID NO:21 contain linkers comprising the base sequences of SEQ ID NO:22 and SEQ ID NO:23 below.

```
                                           SEQ ID NO: 22
                    5'-GGTGGTTCT-3';

SEQ ID NO: 23
                    5'-GGATCCGGTGGC-3';
```

The r5M-172PG1173, r5M-172PMAP36173 or r5M-172(PG1)₃173 was inserted into the NdeI and XhoI restriction enzyme sites of the pET30b expression vector to give a recombinant expression vector.

The amino acid sequence of r5M-172(PG1)₃173 is SEQ ID NO:24 below. During the separation of the antimicrobial peptide PG1 therefrom, the amino acid bond is cleaved between aspartic acid and proline in the Asp-Pro bond upon acid treatment using HCl, whereby the antimicrobial peptide may be isolated.

```
(5' → 3')
                                           SEQ ID NO: 24
MHHHHHHQSKGEELFTGVVPILVELDGDVNGHKFSVRGEGEGDATNGK

LTLKFICTTGKLPVPWPTLVTTLGYGVQCFARYPSHIKRHDFFKSALP

EGYVQERTISFKDDGTYKTRAEVKFEGDTLVNRIELKGIDFKEDGNIL

GHKLEYNFNSHKVYITADKQKNGIKANFKIRHNVEGGSGTDPRGGRLC

YCRRRFCVCVGRGDPRGGRLCYCRRRFCVCVGRGDPRGGRLCYCRRRF

CVCVGRGDPGSGGDGSVQLADHYQQNTPIGDDNHYLSTQSVLLKSPNE

KRDHAVLLEFVTAAGITHGKDELYKHHHHHH;
```

EXAMPLE 2

Incubation of *E. coli* Transformant and Induction of Fusion Protein Expression

The recombinant expression vector obtained in Example 1 was introduced into *E. coli* BL21 and then incubated in 1 L of an LB (Luria-Bertani) medium at 37° C., and the protein expression was induced by adding 0.1 mM IPTG (Isopropyl (3-D thiogalactoside). Protein expression was induced until the turbidity of the broth, that is, OD600 (which is the optical density at 600 nm of the light wavelength), reached 0.6 to 0.8, after which expression was further induced for 5 hr.

EXAMPLE 3

Separation of Insoluble Fusion Protein

The broth in which the expression was induced in Example 2 was centrifuged at 4° C. and 8000 rpm for 10 min, thus recovering E. coli cells. The recovered cells were disrupted using a sonicator, and the disrupted cell lysate was centrifuged at 4° C. and 13000 rpm for 20 min, thus obtaining a soluble fraction and a pellet containing an insoluble protein. The insoluble pellet was resuspended in 40 ml/L of a lysis buffer (pH 7.4 20 mM sodium phosphate buffer including 100 mM sodium chloride, 0.5% triton-X100, 0.1 mM PMSF, 1 mM DTT). Thereafter, the lysate was added with lysozyme (0.1 mg/ml) and DNase (0.01 mg/ml) and then incubated at room temperature for 20 min. In this procedure, the cell walls were destroyed by the lysozyme and DNA was cleaved with the DNase.

Thereafter, the lysate including the lysozyme and the DNase was centrifuged at 4° C. and 8000 rpm for 10 min, thus obtaining an insoluble protein expressed in the form of inclusion bodies. In order to increase the yield of the obtained insoluble protein, a washing step for removing cell walls, cell debris, and gDNA was performed two times using a sodium phosphate buffer including the lysozyme and the DNase.

Next, the insoluble protein was resuspended in a pH 7.4 20 mM sodium phosphate buffer including 8 M urea and 30 mM imidazole and then purified through Ni-NTA column chromatography (GE Healthcare Bio-Sciences, Sweden).

The fraction eluted after purification was analyzed through SDS-PAGE and dialyzed using deionized water as a dialysis solution at room temperature.

EXAMPLE 4

Separation and Purification of Antimicrobial Peptide PG1, PMAP36

The insoluble protein, dialyzed after purification in Example 3, was freeze-dried and dissolved in 70% formic acid.

The insoluble protein solution produced from the transformant including the recombinant gene r5M-172PG1173 or r5M-172PMAP36173 was added with a cyanogen bromide (CNBr) solution and then incubated in a dark room for 24 hr, whereby the N-terminus and the C-terminus of GFP positioned at both ends of the antimicrobial peptide PG1 or PMAP36 were cleaved. The formic acid and cyanogen bromide were removed through freeze-drying and lysed using a buffer for reverse-phase HPLC.

In order to purify the antimicrobial peptide PG1 from r5M-172(PG1)$_3$173, an amino acid cleavage process was performed under acidic conditions. This is because conventional cyanogen bromide must be used carefully due to the high toxicity thereof and thus the processing speed is slow, and also it is expensive, thus negating economic benefits.

The insoluble protein produced from the transformant including the recombinant gene r5M-172(PG1)$_3$173 was configured such that PG1 was continuously arranged in the form of three copies in accordance with Example 1 and such that the Asp-Pro (aspartic acid-proline, DP) amino acid sequence was connected to the N-terminus or C-terminus of each of the PG1 copies or the linkage portion thereof. The insoluble protein was treated at 75° C. for 4 hr using 80 mM HCl, and thus the Asp-Pro amino acid bond was cleaved, whereby PG1 was separated from the insoluble protein.

The purity of the purified protein was analyzed at individual steps through 16% tris-tricine SDS-PAGE.

The antimicrobial peptides PG1 and PMAP36 were purified through reverse-phase HPLC (Waters Deltapak C18 column 7.8, 300 mm), and a sample was allowed to flow at a rate of 2.5 ml/min for 1 hr into a tube containing 0.1% trifluoroacetic acid in which acetonitrile had a linear gradient concentration of 5 to 90%. The absorbance was observed at both 220 nm and 280 nm, and the matching peak was analyzed through 16% tris-tricine SDS-PAGE.

The purified fraction was freeze-dried to remove the unnecessary buffer to create refolding conditions, and was then refolded to the native state by the addition of a refolding buffer composed of a 20 mM sodium phosphate buffer (pH 7.4) including 8 M urea, 5 mM reduced glutathione and 0.5 mM oxidized glutathione, and simultaneously, the refolding buffer was replaced with deionized water through dialysis. Thereafter, the purified and dialyzed peptide was freeze-dried.

TEST EXAMPLE 1

Measurement and Comparison of Growth Curves of E. coli BL21 in Which Protein Expression of pET30b Expression Vector Inserted with r5M-172PG1173 Gene was Induced and Was Not Induced The results of growth of E. coli BL21, in which the r5M172-PG1-173 protein expression was induced and was not induced in E. coli BL21 into which the pET30b expression vector inserted with r5M172-PG1-173 gene was introduced, were compared through measurement of optical density.

As shown in FIG. 3, the r5M-172PG1173 protein expression did not greatly affect the growth rate of E. coli. The antimicrobial peptide inserted into the insoluble GFP scaffold has no significant influence on the growth of E. coli. As shown in FIG. 4, the r5M-172PG1173 protein was expressed in the form of inclusion bodies.

In order to realize the stable production of the antimicrobial peptide, many attempts have been made to bind to fusion partners, but low production yields have resulted, and thus there is the need for supplementary measures that incur additional production costs, including the addition of a nutrient-rich medium, insertion of multiple gene copies between fusion partners, etc. However, the fusion protein according to the present invention, prepared merely by inserting the antimicrobial peptide into GFP, which is highly expressed in an insoluble state, can produce the antimicrobial peptide with high yield by minimizing the growth inhibition of host cells.

TEST EXAMPLE 2

Measurement of Protein Productivity Over Time of pET30b Expression Vector Inserted with r5M-172PG1173 Gene The r5M-172PG1173 protein production over time (3 h, 4 h, 5 h) of the pET30b expression vector inserted with r5M-172PG1173 gene in E. coli was confirmed through sodium dodecyl sulfate-polyacrylamide gel electrophoresis (SDS-PAGE) using a whole-cell protein sample.

Consequently, as shown in FIG. 5, in lanes in which protein expression was induced (3 h, 4 h, 5 h), unlike the lane in which r5M-172PG1173 protein expression was not induced (UI), the r5M-172PG1173 protein was obviously expressed for 3 to 5 hr in *E. coli* BL21.

TEST EXAMPLE 3

Measurement of Protein Productivity of r5M-172PG1173 and r5M-172PMAP36173 in pET30b Expression Vector Introduced into *E. coli* BL21

Each of PG1 gene and PMAP36 gene inserted into the r5M-GPF gene was cloned into the pET30b expression vector, after which the expression thereof was induced in *E. coli* BL21 for 5 hr.

The recombinant protein is expected to constitute about 45 to 50% of the total intracellular protein content. 1.4 g of the obtained r5M-172PG1173 insoluble protein (31 kDa) for 1 L of the cell broth and 1.3 g of the obtained r5M-172PG1173 insoluble protein (33 kDa) for 1 L of the cell broth eventually accounted for almost 90% of the target protein, as shown in the final insoluble electrophoresis fraction (FIGS. 6A and 6B).

The insoluble protein was purified through Ni-NTA chromatography, and the purified target protein was pooled and dialyzed with deionized water as a dialysis solution.

TEST EXAMPLE 4

Measurement of Yield of Antimicrobial Peptides PG1 and PMAP36

PG1 and PMAP36 were each cleaved from r5M-GPF in the protein sample dialyzed in Test Example 3, after which PG1 (2.4 kDa) and PMAP36 (4.2 kDa) were purified through HPLC, and then the yields thereof were measured.

Consequently, as shown in Table 5 below, the protein produced from the recombinant (r5M-172(PG1)$_3$173) including three copies of PG1 was exhibited at a yield of about 2.3 times.

TABLE 5

| Purification steps | Yield (mg/L) | | |
|---|---|---|---|
| | PG1 | PMAP36 | (PG1)$_3$[a] |
| Total Insoluble protien[b] | ~1400 | ~1300 | ~1350 |
| Ni-NTA Purification[b] | ~250 | ~220 | ~241 |
| RP-HPLC[c] | 12 to 14 | 9 to 12 | 27 to 29 |

[a]Three copies of PG-1 was inserted in the scaffold of r5M-GFP
[b]Determined by Braford assay
[c]Freeze-dried protien samples were mesured by microbalance

TEST EXAMPLE 5

Analysis of Purity of Antimicrobial Peptides PG1 and PMAP36

In order to obtain high-purity PG1 and PMAP36, the protein sample extracted in each protein purification step was loaded through tris-tricine SDS-PAGE, followed by electrophoresis and purity analysis, thereby obtaining the antimicrobial peptides PG1 and PMAP36 having a purity of 95% or more (FIGS. 7A and 6B).

Also, the purified PG1 was subjected to western blot assay using anti-PG1 antibody. As shown in FIG. 7C, PG1 was easily observed at 2.4 kDa.

Although specific embodiments of the present invention have been disclosed in detail as described above, it will be obvious to those skilled in the art that such description is merely of preferable exemplary embodiments and is not to be construed to limit the scope of the present invention. Therefore, the substantial scope of the present invention will be defined by the appended claims and equivalents thereof.

---

The invention claimed is:

1. An insoluble fusion protein, comprising the amino acid sequence of SEQ ID NO:24.

2. An isolated polynucleotide encoding the insoluble fusion protein of claim 1 and comprising the sequence of SEQ ID NO:21.

3. A recombinant expression vector, comprising the polynucleotide of claim 2.

4. A transformant comprising the recombinant expression of claim 3 which is introduced into a host cell.

5. The transformant of claim 4, wherein the host cell is *Escherichia coli*.

6. A method of producing an antimicrobial peptide, comprising:
  (1) incubating a recombinant transformant comprising a base sequence of SEQ ID NO:21 in a culture medium;
  (2) recovering the transformant from the culture medium;
  (3) obtaining a protein from the transformant; and
  (4) subjecting the protein to acid treatment to thus separate the antimicrobial peptide.

7. The method of claim 6, wherein the protein is expressed in a form of inclusion bodies.

8. The method of claim 6, wherein the antimicrobial peptide is arranged continuously, and comprises an Asp-Pro amino acid sequence at the N-terminus or C-terminus of the continuously arranged antimicrobial peptide.

9. The method of claim 8, wherein the Asp-Pro amino acid sequence is cleaved through acid treatment.

10. The method of claim 9, wherein the acid treatment is performed by adding HCl.

11. The method of claim 8, wherein the continuously arranged antimicrobial peptide is present in three copies.

\* \* \* \* \*